United States Patent [19]

Cotrel et al.

[11] 4,038,391
[45] July 26, 1977

[54] 6-(1,8-NAPHTHYRIDIN-2-YL)-5-PIPERAZINO CARBONYLOXY-7-OXO-6,7-DIHYDRO-5H-PYRROLO-[3,4-b]PYRAZINES AND RELATED PYRIDINES

[75] Inventors: Claude Cotrel, Paris; Cornel Crisan, Sceaux; Claude Jeanmart, Brunoy; Mayer Naoum Messer, Bievres, all of France

[73] Assignee: Rhone-Poulenc S.A., Paris, France

[21] Appl. No.: 623,358

[22] Filed: Oct. 17, 1975

Related U.S. Application Data

[62] Division of Ser. No. 469,431, May 13, 1974, abandoned.

[30] Foreign Application Priority Data

May 15, 1973 France ................. 73.17516
Mar. 14, 1974 France ................. 74.08728
Mar. 14, 1974 France ................. 74.08730

[51] Int. Cl.² .................. A61K 31/495; C07D 471/04
[52] U.S. Cl. .............................. 424/250; 260/268 BC
[58] Field of Search ................ 424/250; 260/268 BC

[56] References Cited
PUBLICATIONS

Cotrel et al. Chemical Abstracts vol. 79, 92,284c, (1973).
Challier et al. Chemical Abstracts vol. 79, 32,100e, (1973).

*Primary Examiner*—Donald G. Daus
*Assistant Examiner*—Jose Tovar

*Attorney, Agent, or Firm*—Stevens, Davis, Miller & Mosher

[57] ABSTRACT

Compounds of the formula:

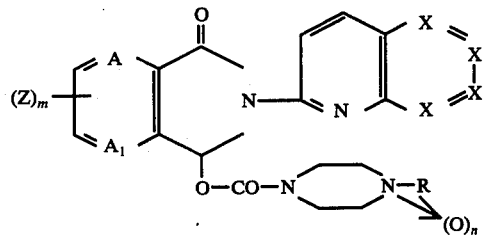

wherein one of the symbols =X- represents =N- and the other three each represent a group

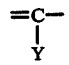

in which Y represents hydrogen, halogen, alkyl, alkoxy, cyano or nitro, =A- and =A$_1$- represent a group =CH- or =N-, =A$_1$- representing a group =CH- or =N- when =A- represents =CH- and =A$_1$- representing =N- when A represents =N-, Z represents hydrogen, halogen, alkyl, alkoxy or nitro, *m* represents zero or an integer from 1 to 4, and (i) *n* represents zero and R represents hydrogen, alkyl, alkenyl, alkynyl, hydroxyalkyl or phenyl, or (ii) *n* represents 1 and R represents alkyl, hydroxyalkyl or phenyl, are new compounds possessing pharmacological properties; they are particularly active as tranquilizers and anticonvulsant agents.

11 Claims, No Drawings

6-(1,8-NAPHTHYRIDIN-2-YL)-5-PIPERAZINO CARBONYLOXY-7-OXO-6,7-DIHYDRO-5H-PYRROLO-[3,4-b]PYRAZINES AND RELATED PYRIDINES

This is a division of application Ser. No. 469,431 filed May 13, 1974 now abandoned.

This invention relates to new therapeutically useful naphthyridine derivatives, to processes for their preparation and pharmaceutical compositions containing them.

The new naphthyridine derivatives of the present invention are those of the general formula:

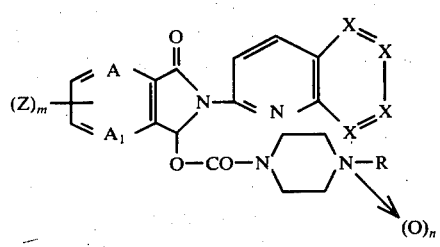

I wherein one of the symbols =X— represents =N— and the other three each represent a group

in which Y represents a hydrogen or halogen (preferably chlorine or bromine) atom, an alkyl radical containing 1 to 4 carbon atoms (preferably methyl), an alkoxy radical containing 1 to 4 carbon atoms (preferably methoxy), or a cyano or nitro radical, the symbols =A— and =A$_1$— represent a group =CH— or =N—, =A$_1$—representing a group =CH— or =N— when =A— represents =CH— and =A$_1$— representing =N— when A represents =N—, the symbol Z represents a hydrogen or halogen atom, an alkyl or alkoxy radical containing 1 to 4 carbon atoms, or the nitro radical, m represents zero or an integer from 1 to 4 (preferably zero), and (i) n represents zero and R represents a hydrogen atom, an alkyl radical containing 1 to 4 carbon atoms (e.g. ethyl, isopropyl, t.-butyl or, more especially, methyl), an alkenyl radical containing 2 to 4 carbon atoms (e.g. allyl), an alkynyl radical containing 2 to 4 carbon atoms (e.g. propargyl), a hydroxyalkyl radical containing 1 to 4 carbon atoms (e.g. 2-hydroxyethyl) or a phenyl radical, or (ii) n represents 1 and R represents an alkyl or hydroxyalkyl radical containing 1 to 4 carbon atoms, or a phenyl radical, and acid addition salts thereof. It is to be understood that the symbols Y of the three groups

represented by symbol X in the above formula may represent the same or different atoms or radicals as stated above, and when symbol m represents the integer 2, 3 or 4 the atoms or radicals attached to the carbon atoms of the ring may be the same or different.

According to a feature of the invention, the compounds of general formula I wherein n represents zero are prepared by the process which comprises reacting a chlorocarbonylpiperazine of the general formula:

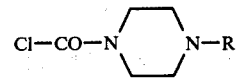

II (wherein R represents a hydrogen atom or an alkyl, alkenyl, alkynyl, hydroxyalkyl or phenyl radical) with a naphthyridine derivative of the general formula:

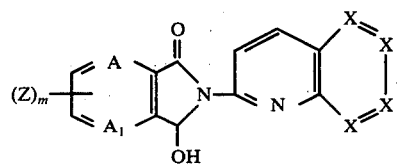

III wherein X, A, A$_1$, Z and m are as hereinbefore defined.

Generally, a compound of general formula II is reacted with an alkali metal salt, optionally prepared in situ, of a compound of general formula III, the reaction being carried out in an anhydrous organic solvent, e.g. dimethylformamide or tetrahydrofuran, at a temperature below 60° C.

The reaction can also be carried out by reacting an acid addition salt of a compound of general formula II, preferably the hydrochloride, with a compound of general formula III, working in pyridine and optionally in the presence of a tertiary amine (e.g. triethylamine) which liberates the compound of general formula II from its salt.

The naphthyridine derivatives of general formula III can be obtained by partial reduction of an imide of the general formula:

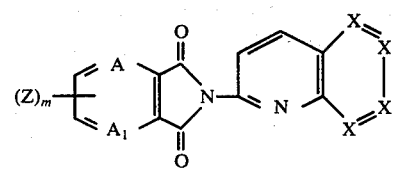

IV (wherein X, A, A$_1$, Z and m are as hereinbefore defined) to convert one of the carbonyl groups to a hydroxymethylene group.

The reduction is generally carried out by means of an alkali metal borohydride in organic or aqueous-organic solution, such as a mixture of dioxan and methanol or a mixture of dioxan and water or a mixture of methanol and water or a mixture of ethanol and water.

The partial reduction of an imide of general formula IV can lead to isomeric products which can be separated by physico-chemical methods such as fractional crystallisation or chromatography.

The imides of general formula IV can be prepared by reacting a 2-aminonaphthyridine of the general formula:

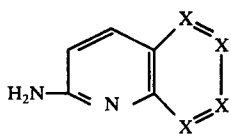

(wherein X is as hereinbefore defined) with an anhydride of the general formula:

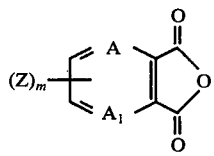

VI (wherein A, A₁, Z and m are as hereinbefore defined), optionally forming as an intermediate a product of the general formula:

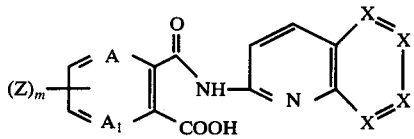

VII wherein X, A, A₁, Z and m are as hereinbefore defined.

The reaction of the 2-aminonaphthyridine of general formula V with the anhydride of general formula VI is generally carried out by heating in an organic solvent, for example acetic acid, dimethylformamide, acetonitrile or diphenyl ether.

The cyclisation of the intermediate product of general formula VII to form an imide product of general formula IV can generally be effected either by heating with acetyl chloride in acetic acid or acetic anhydride, or by the action of a condensation agent such as N,N'-dicyclohexyl-carbodiimide in dimethylformamide at a temperature of about 20° C.

According to another feature of the invention, the compounds of general formula I wherein n is zero or 1 and R has the corresponding meanings given above are prepared by the process which comprises reacting a piperazine of the general formula:

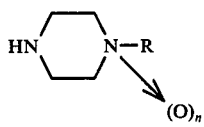

VIII (wherein n is zero or 1 and R is as hereinbefore defined) with a mixed carbonate of the general formula:

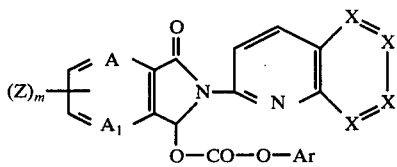

IX wherein X, A, A₁, Z and m are as hereinbefore defined, and Ar represents a phenyl radical optionally substituted by an alkyl radical containing 1 to 4 carbon atoms or a nitro radical. The reaction is generally carried out in an anhydrous organic solvent, e.g. acetonitrile or dimethylformamide, at a temperature of about 20° C., e.g. 15° to 25° C.

The piperazine compound of general formula VIII wherein n represents 1 and R represents the methyl radical and its dihydrochloride can be obtained by oxidation of t.-butyl (4-methylpiperazin-1-yl)carboxylate by means of 4-nitroperbenzoic acid in anhydrous chloroform at a temperature not exceeding 40° C., followed by replacement of the t.-butoxycarbonyl group by a hydrogen atom by heating 1-methyl-4-t.-butoxycarbonyl-piperazine-1-oxide hydrochloride under reflux in an ethanolic medium in the presence of anhydrous hydrochloric acid. The other piperazine compounds of general formula VIII can be obtained in a similar manner.

The mixed carbonates of general formula IX can be prepared by reacting a chloroformate of the general formula:

$$Cl - CO - O - Ar \qquad X$$

(wherein Ar is as hereinbefore defined) with a naphthyridine derivative of general formula III. The reaction is generally carried out in a basic organic solvent, e.g. pyridine, at a temperature between 0° and 20° C.

According to another feature of the invention, the compounds of general formula I wherein n represents 1 and R represents an alkyl, hydroxyalkyl or phenyl radical are obtained by the process which comprises the oxidation of a corresponding compound of general formula I wherein n represents zero and R is as defined above. The oxidation is generally carried out by means of an organic peracid, e.g. 3-chloroperbenzoic acid or 4-nitroperbenzoic acid, in an organic solvent, e.g. chloroform, and at a temperature of about 20° C.

The naphthyridine derivatives of general formula I obtained by the aforementioned processes can be purified by physical methods such as distillation, crystallisation or chromatography, or by chemical methods such as the formation of salts, crystallisation of the salts and decomposition of them in an alkaline medium. In carrying out the said chemical methods the nature of the anion of the salt is immaterial, the only requirement being that the salt must be well-defined and readily crystallisable.

The naphthyridine derivatives of general formula I may be converted by methods known per se into acid addition salts. The acid addition salts may be obtained by the action of acids on the naphthyridine derivatives in appropriate solvents. As organic solvents there may be used alcohols, ethers, ketones or chlorinated hydrocarbons. The salt which is formed is precipitated, if necessary after concentration of the solution, and is isolated by filtration or decantation.

The naphthyridine derivatives of the invention and their acid addition salts possess valuable pharmacological properties; they are particularly active as tranquillisers and anti-convulsant agents. In animals (mice) they have proved active as such at doses of between 0.1 and 100 mg./kg. animal body weight when administered orally, in particular in the following tests:

i. electric battle test according to a technique similar to that of Tedeschi et al [J. Pharmacol., 125, 28 (1959)], ii. convulsion with pentetrazole according to a technique similar to that of Everett and Richards [J. Pharmacol., 81, 402 (1944)], iii. supramaximal electroshock according to the technique of Swinyard et al [J. Pharmacol., 106, 319 (1952)], and iv. locomotor activity according to the technique of Courvoisier [Congrès des Medècins, Aliènistes et Neurologistes - Tours - (8/13th June 1959)] and Julou (Bulletin de la Societe de Pharmacie de Lille, No. 2, Jan. 1967, p. 7).

Furthermore, they exhibit only low toxicity; their 50% lethal dose ($LD_{50}$) in the case of mice is generally greater than 300 mg./kg. animal body weight when administered orally.

The naphthyridine derivatives of the general formula:

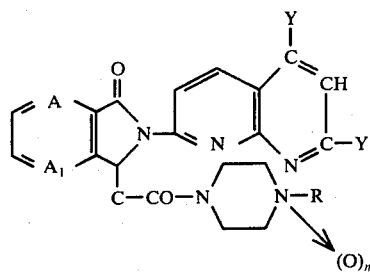

XI wherein the symbols Y, which may be the same or different, each represent a hydrogen or halogen atom, or an alkyl or alkoxy radical containing 1 to 4 carbon atoms, or a cyano radical, =A- and =A$_1$- represent a group =CH- or =N-, =A$_1$- representing =CH- or =N- when =A- represents =CH- and A$_1$ representing =N- when =A- represents =N-, and n represents zero and R represents an alkyl radical containing 1 to 4 carbon atoms (preferably methyl), an alkenyl radical containing 2 to 4 carbon atoms, an alkynyl radical containing 2 to 4 carbon atoms or a hydroxyalkyl radical containing 1 to 4 carbon atoms, or n represents 1 and R represents the methyl radical, and their acid addition salts, are of very particular interest. Of outstanding value are the compounds 2-(7-bromo-1,8-naphthyridin-2-yl)-3-(4-methylpiperazin-1-yl)carbonyloxy-isoindolin-1-one, 2-(7-cyano-1,8-naphthyridin-2-yl)-3-(4-methylpiperazin-1-yl)carbonyloxy-isoindolin-1-one, 2-(7-chloro-1,8-naphthyridin-2-yl)-3-[4-(2-hydroxyethyl)-piperazin-1-yl]carbonyloxy-isoindolin-1-one, 3-(4-allyl-piperazin-1-yl)carbonyloxy-2-(7-chloro-1,8-naphthyridin-2-yl)isoindolin-1-one, 2-(7-chloro-1,8-naphthyridin-2-yl)-3-(4-ethylpiperazin-1-yl)carbonyloxy-isoindolin-1-one, 2-(7-chloro-1,8-naphthyridin-2-yl)-3-(4-propargylpiperazin-1-yl)carbonyloxy-isoindolin-1-one, 2-(7-chloro-1,8-naphthyridin-2-yl)-3-(4-t.-butylpiperazin-1-yl)carbonyloxy-isoindolin-1-one, 4-{2-(7-chloro-1,8-naphthyridin-2-yl)-3-oxo-isoindolin-1-yl]oxycarbonyl}-1-methylpiperazine-1-oxide, 6-(7-chloro-1,8-naphthyridin-2-yl)-5-(4-methylpiperazin-1-yl)carbonyloxy-7-oxo-6,7-dihydro-5H-pyrrolo[3,4-b]pyrazine and, more especially, 2-(7-chloro-1,8-naphthyridin-2-yl)-3-(4-methylpiperazin-1-yl)carbonyloxy-isoindolin-1-one, and their acid addition salts.

For therapeutic purposes, the naphthyridine derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-8-hydroxynaphthoates) so that the beneficial physiological properties inherent in the bases are not vitiated by side-effects ascribable to the anions.

The following Examples illustrate the preparation of naphthyridine derivatives of this invention.

EXAMPLE 1

Sodium hydride (50% dispersion in mineral oil) (2.1 g.) is added all at once to a suspension of 2-(7-chloro-1,8-naphthyridin-2-yl)-3-hydroxy-isoindolin-1-one (12.4 g.) in anhydrous dimethylformamide (125 cc.) whilst cooling externally with an ice bath. When the evolution of gas has ceased, a solution of 1-chlorocarbonyl-4-methylpiperazine (11.3 g.) in anhydrous dimethylformamide (110 cc.) is added, the external cooling being maintained. After the end of the addition, the reaction mixture is stirred for 14 hours at 0° C., and then for 6 hours at 22° C. The reaction mixture is then poured onto ice (800 g.). The product which crystallises is filtered off, washed with water (240 cc.) and dried in air to yield a crude product (13 g.) which melts at about 210° C. On recrystallisation from acetonitrile (900 cc.), 2-(7-chloro-1,8-naphthyridin-2-yl)-3-(4-methylpiperazin-1-yl)carbonyloxy-isoindolin-1-one (8.5 g.), melting at 204° C., is obtained.

2-(7-Chloro-1,8-naphthyridin-2-yl)-3-hydroxy-isoindolin-1-one can be prepared by adding potassium borohydride (1.72 g.) to a suspension of 2-(7-chloro-1,8-naphthyridin-2-yl)phthalimide (17.7 g.) in dioxan (87 cc.) and a saturated aqueous solution of disodium phosphate (26.4 cc.), whilst cooling externally with an ice bath. After stirring for 14 hours, the mixture is allowed to return to a temperature of about 20° C., stirring is carried out for a further 2 hours, and then a saturated aqueous solution of disodium phosphate (400 cc.) is added. The precipitate which forms is filtered off and washed with cold water (225 cc.). After drying in air, 2-(7-chloro-1,8-naphthyridin-2-yl)-3-hydroxy-isoindolin-1-one (17.5 g.), melting at 248° C., is obtained.

2-(7-Chloro-1,8-naphthyridin-2-yl)phthalimide can be prepared by heating a mixture of 2-(7-hydroxy-1,8-naphthyridin-2-yl)phthalimide (26.3 g.) with phosphorus oxychloride (79 cc.) and dimethylformamide (3.5 cc.) under reflux until the evolution of gas ceases. After cooling, the reaction mixture is poured into ice-water (650 cc.) without exceeding 25° C. The product obtained is filtered off, washed with water (150 cc.) and dried to constant weight to give 2-(7-chloro-1,8-naphthyridin-2-yl)phthalimide (24.1 g.) melting at 268° C.

2-(7-Hydroxy-1,8-naphthyridin-2-yl)phthalimide can be prepared by heating a mixture of 2-amino-7-hydroxy-1,8-naphthyridine (25 g.) with phthalic anhydride (70 g.) in acetic acid (1,400 cc.) under reflux for 3 hours. After cooling, an insoluble material is filtered off. The crystals obtained are filtered off, washed successively with diethyl ether (60 cc.), water (90 cc.), a saturated solution of sodium bicarbonate (120 cc.) and finally water (60 cc.). The crystals are dried to constant weight and 2-(7-hydroxy-1,8-naphthyridin-2-yl)phthalimide (17 g.), melting at 370° C., is thus obtained.

2-Amino-7-hydroxy-1,8-naphthyridine can be prepared according to the method described by S. Carboni et al, Gazz. Chim. Ital., 95, 1498 (1965).

EXAMPLE 2

Triethylamine (5.6 cc.) followed by anhydrous pyridine (25 cc.) are added to a suspension of 2-(7-chloro-1,8-naphthyridin-2-yl)-3-hydroxy-isoindolin-1-one (3.12 g.) and 1-chlorocarbonyl-4-methylpiperazine hydrochloride (5.97 g.) in methylene chloride (50 cc.), whilst keeping the temperature at about 25° C. The reaction mixture is then heated at a temperature of about 50° C. for 1 hour and is then stirred for 18 hours at a temperature of about 20° C. Methylene chloride (50 cc.) and water (100 cc.) are then added. The aqueous layer is decanted and then washed three times with methylene chloride (50 cc.). The organic layers are combined and washed with water (50 cc.), dried over anhydrous sodium sulphate and then concentrated to dryness under reduced pressure. On recrystallisation of the resulting residue from acetonitrile (100 cc.), 2-(7-chloro-1,8-naphthyridin-2-yl)-3-(4-methylpiperazin-1-yl)carbonyloxy-isoindolin-1-one (2.5 g.), melting at 203° C., is obtained.

EXAMPLE 3

A suspension of sodium hydride (50% dispersion in mineral oil) (1.46 g.) in anhydrous dimethylformamide (80 cc.) is added to a suspension of 3-hydroxy-2-(1,5-naphthyridin-2-yl)isoindolin-1-one (7 g.) in anhydrous dimethylformamide (410 cc.). When the evolution of gas has ceased, a solution of 1-chlorocarbonyl-4-methyl-piperazine (4.6 g.) in anhydrous dimethylformamide (25 cc.) is added dropwise. After stirring for 4 hours, the reaction mixture is poured into water (3,000 cc.) cooled to 13° C. The precipitate is filtered off, washed with water (75 cc.) and then dried to yield 3-(4-methylpiperazin-1-yl)carbonyloxy-2-(1,5-naphthyridin-2-yl) isoindolin-1-one (5.7 g.) melting at 170°–171° C. After recrystallisation from acetonitrile (50 cc.), the products melts at 173° C.

3-Hydroxy-2-(1,5-naphthyridin-2-yl)isoindolin-1-one can be prepared by adding potassium borohydride (0.91 g.) to a suspension of 2-(1,5-naphthyridin-2-yl)-phthalimide (6.2 g.) in dioxan (57 cc.) and a saturated aqueous solution of disodium phosphate (11.1 cc.) cooled to 10° C. The mixture is then allowed to return to a temperature of about 20° C. After 2 hours, a saturated aqueous solution of disodium phosphate (105 cc.) is added. The precipitate is filtered off, washed with distilled water (300 cc.) and then dried to yield 3-hydroxy-2-(1,5-naphthyridin-2-yl)isoindolin-1-one (4.8 g.) melting at 208° C.

2-(1,5-Naphthyridin-2-yl)phthalimide can be prepared by heating 2-amino-1,5-naphthyridine (20 g.) with phthalic anhydride (20.4 g.) in dimethylformamide (138 cc.) for 40 minutes at 145° C. After cooling, distilled water (550 cc.) is added. The precipitate is filtered off and then washed with water (150 cc.). 2-(1,5-Naphthyridin-2-yl)phthalimide (17.5 g.), melting at 206° C., is thus obtained.

2-Amino-1,5-naphthyridine can be prepared according to W. Czuba, Rec. Trav. Chim., 82, 988 (1963).

EXAMPLE 4

Sodium hydride (50% dispersion in mineral oil) (0.8 g.) is added to a suspension of 2-(7-methoxy-1,8-naphthyridin-2-yl)-3-hydroxy-isoindolin-1-one (4.63 g.) in anhydrous dimethylformamide (45 cc.), whilst keeping the temperature between 18°–20° C. The reaction mixture is stirred for a further 4 hours 30 minutes. A solution of 1-chlorocarbonyl-4-methylpiperazine (2.7 g.) in anhydrous dimethylformamide (25 cc.) is then added over the course of 15 minutes and at a temperature of 20° C. The suspension is stirred for 17 hours at a temperature of about 20° C., and then anhydrous hexamethylphosphotriamide (7 cc.) is added. After 15 minutes, the reaction mixture is poured into ice-water (500 g.). The precipitate is filtered off and washed with water (45 cc.). A product (6.1 g.) is obtained and is recrystallised from diisopropyl ether (1,500 cc.). 2-(7-Methoxy-1,8-naphthyridin-2-yl)-3-(4-methylpiperazin-1-yl)carbonyloxy-isoindolin-1-one (3 g.), melting at 191° C., is thus obtained.

The 2-(7-methoxy-1,8-naphthyridin-2-yl)-3-hydroxy-isoindolin-1-one can be prepared in the following way:

Preparation of 2-acetylamino-7-chloro-1,8-naphthyridine, m.p. 251°–253° C., according to S. Carboni et al [Gazz. Chim. Ital., 95, 1492 (1965)].

Preparation of 2-amino-7-methoxy-1,8-naphthyridine (1.0 g.), m.p. 156° C., by reacting sodium methoxide (1.8 g.) with 2-acetylamino-7-chloro-1,8-naphthyridine (2.2 g.) in anhydrous methanol (40 cc.) under reflux for 45 minutes. Preparation of 2-(7-methoxy-1,8-naphthyridin-2-yl)-phthalimide (20 g.), m.p. 295° C., by reacting phthalic anhydride (10 g.) with 2-amino-7-methoxy-1,8-naphthyridine (12 g.) in diphenyl ether (240 cc.) for 10 minutes at 160° C.

Preparation of 2-(7-methoxy-1,8-naphthyridin-2-yl)-3-hydroxy-isoindolin-1-one (18.6 g.), m.p. 218° C., by reacting potassium borohydride (3.55 g.) with 2-(7-methoxy-1,8-naphthyridin-2-yl)phthalimide (20 g.) in dioxan (200 cc.) and a saturated aqueous solution of disodium phosphate (40 cc.) for 4 hours at a temperature of about 20° C.

EXAMPLE 5

The procedure described in Example 4 is followed but starting with 2-(7-bromo-1,8-naphthyridin-2-yl)-3-hydroxy-isoindolin-1-one (8 g.) in anhydrous dimethylformamide (240 cc.), sodium hydride (50% dispersion in mineral oil) (1.2 g.) and 1-chlorocarbonyl-4-methylpiperazine (4.1 g.) in anhydrous dimethylformamide (40 cc.). After stirring at 26° C. for 18 hours, the reaction mixture is poured into ice-water (1,500 cc.). The insoluble matter (7.3 g.) is filtered off and dissolved in a mixture (73 cc.) of methylene chloride and ethyl acetate (80–20 by volume). The solution obtained is passed through a column of silica gel (73 g.). Elution is first carried out with a mixture (5,750 cc.) of methylene chloride and ethyl acetate (80–20 by volume); the corresponding eluates ae discarded. Elution is then carried out with pure ethyl acetate (1,250 cc.) and then with a mixture (1,250 cc.) of ethyl acetate and methanol (50—50 by volume); the corresponding eluates are combined and concentrated to dryness. A residue (3 g.) is obtained which is dissolved in ethanol (90 cc.). A solution of oxalic acid (0.53 g.) in ethanol (10.5 cc.) is added to the solution obtained. The mixture is stirred for 1 hour and the precipitate which forms is filtered off and washed with ethanol (6 cc.). A product (1.8 g.), melting at 260° C., is thus obtained and is treated with a saturated solution of sodium bicarbonate (50 cc.) and methylene chloride (40 cc.). The organic layer is isolated by decanting, dried over anhydrous potassium carbonate and concentrated to dryness. A residue weighing 1.2 g. is obtained and is recrystallised from ethanol (80 cc.). 2-(7-Bromo-1,8-naphthyridin-2-yl)-3-(4-methylpiperazin-1yl)carbonyloxy-isoindolin-1-one (0.9 g.), melting at 225°–230° C., is thus obtained.

2-(7-Bromo-1,8-naphthyridin-2-yl)-3-hydroxyisoindolin-1-one can be prepared in the following way: Preparation of 2-(7-bromo-1,8-naphthyridin-2-yl)phthalimide (23.6 g.), m.p. 265° C., by heating a mixture of 2-(7-hydroxy-1,8-naphthyridin-2-yl)phthalimide (20.5 g.) and phosphorus pentabromide (30.3 g.) in bromoform (205 cc.) and dimethylformamide (7 cc.) for 1 hour at a temperature of about 100° C.

Preparation of 2-(7-bromo-1,8-naphthyridin-2-yl)-3-hydroxy-isoindolin-1-one (8.2 g.), m.p. 264° C., from 2-(7-bromo-1,8-naphthyridin-2-yl)phthalimide (10.6 g.) and potassium borohydride (1.2 g.) in a mixture (200 cc.) of methanol and dioxan (50—50 by volume) at a temperature of about 20° C.

EXAMPLE 6

Following the procedure of Example 4 but starting with 2-(7-cyano-1,8-naphthyridin-2-yl)-3-hydroxy-isoindolin-1-one (4.7 g.), sodium hydride (50% dispersion in mineral oil) (1.5 g.), 1-chlorocarbonyl-4-methylpiperazine (5.04 g.), anhydrous tetrahydrofuran (97 cc.) and anhydrous hexamethylphosphotriamide (25 cc.), a crude product (5.7 g.) is obtained which is then dissolved in methylene chloride (100 cc.). The resulting solution is passed through a column of silica gel (57 g.). Elution is carried out successively with methylene chloride (2,400 cc.), ethyl acetate (1,400 cc.) and then a mixture (200 cc.) of ethyl acetate And methanol (50—50 by volume), collecting 200 cc. fractions. The last eight fractions are combined and concentrated to dryness. The residue, weighing 3.4 g., is recrystallised from acetonitrile (250 cc.) to yield 2-(7-cyano-1,8-naphthyridin-2-yl)-3-(4-methylpiperazin-1-yl)carbonyloxy-isoindolin-1-one (2.6 g.) melting at 266°–268° C.

2-(7-Cyano-1,8-naphthyridin-2-yl)-3-hydroxy-isoindolin-1-one can be prepared in the following way:

Preparation of 2-(7-cyano-1,8-naphthyridin-2-yl)phthalimide (7.3 g.), m.p. 320° C., by heating 2-(7-bromo-1,8-naphthyridin-2-yl)phthalimide (17.7 g.) with cuprous cyanide (9 g.) in nitrobenzene (177 cc.) at 160°–165° C. for 1 hour. Insoluble matter is removed by carrying out a hot filtration and the filtrate is then cooled. The product which crystallises is filtered off and then recrystallised from dimethylformamide (70 cc.). Preparation of 2-(7-cyano-1,8-naphthyridin-2-yl)-3-hydroxy-isoindolin-1-one (4.7 g.), m.p. 260° C., from 2-(7-cyano-1,8-naphthyridin-2-yl)phthalimide (5.8 g.) and sodium borohydride (1.04 g.) in methanol (290 cc.) at a temperature between 23 and 27° C.

EXAMPLE 7

Following the procedure of Example 4 but starting with 2-(1,6-naphthyridin-2-yl)-3-hydroxy-isoindolin-1-one (1.7 g.) in anhydrous tetrahydrofuran (17 cc.), sodium hydride (50% dispersion in mineral oil) (0.58 g.), 1-chlorocarbonyl-4-methylpiperazine (0.5 g.) in anhydrous tetrahydrofuran (5 cc.) and hexamethylphosphotriamide (4.5 cc.), a product (1.3 g.), melting at 215° C., is obtained. After washing with diisopropyl ether (30 cc.), this product is dissolved in methylene chloride (40 cc.). After filtration, the solution is concentrated to dryness to yield 3-(4-methylpiperazin-1-yl)carbonyloxy-2-(1,6-naphthyridin-2-yl)isoindolin-1-one (1 g.) melting at 215° C.

2-(1,6-Naphthyridin-2-yl)-3-hydroxy-isoindolin-1-one can be prepared in the following way:

Preparation of 2-amino-1,6-naphthyridine, m.p. 239° C., according to E. M. Hawes and D. K. J. Gorecki, J. Med. Chem., 16, 849 (1973). Preparation of 2-(1,6-naphthyridin-2-yl)phthalimide (2.7 g.), m.p. 265° C., from 2-amino-1,6-naphthyridine (1.45 g.) and phthalic anhydride (1.48 g.) in diphenyl ether (30 cc.) at 180° C. for 3 hours.

Preparation of 2-(1,6-naphthyridin-2-yl)-3-hydroxy-isoindolin-1-one (1.5 g.), m.p. 239° C., from 2-(1,6-naphthyridin-2-yl)phthalimide (2.45 g.) in a mixture (24 cc.) of methanol and dioxan (50—50 by volume) and potassium borohydride (0.4 g.) at 24° C. for 4 hours.

EXAMPLE 8

1-Chlorocarbonyl-4-methylpiperazine (12 g.) is added to a suspension of 5-hydroxy-6-(5-methyl-1,8-naphthyridin-2-yl)-7-oxo-6,7-dihydro-5H-pyrrolo[3,4-b]-pyrazine (7.2 g.) in anhydrous pyridine (123 cc.). The reaction mixture is then heated at a temperature of about 50° C. for 2 hours. After cooling, the suspension obtained is poured into a mixture of water (750 cc.), a saturated aqueous solution of sodium bicarbonate (250 cc.) and methylene chloride (250 cc.). The aqueous layer is decanted and washed four times with methylene chloride (100 cc.). The organic layers are combined, washed four times with water (100 cc.), dried over anhydrous sodium sulphate, filtered and evaporated to dryness under reduced pressure. The residue obtained is dissolved in methylene chloride (50 cc.) and the resulting solution is filtered through silica gel (200 g.) in a column 3.8 cm. in diameter. Elution is carried out with pure methylene chloride (1,000 cc.) and then with a mixture (800 cc.) of methylene chloride and methanol (95—5 by volume). These eluates are discarded. Elution is then carried out with a mixture (1,200 cc.) of methylene chloride and methanol (95—5 by volume); the corresponding eluate is concentrated to dryness under reduced pressure. After recrystallisation of the residue from acetonitrile (40 cc.), 6-(5-methyl-1,8-naphthyridin-2-yl)-5-(4-methylpiperazin-1-yl)-carbonyloxy-7-oxo-6,7-dihydro-5H-pyrrolo[3,4-b]pyrazine (5.1 g.), which melts at 184° C., is obtained.

5-Hydroxy-6-(5-methyl-1,8-naphthyridin-2-yl)-7-oxo-6,7-dihydro-5H-pyrrolo[3,4-b]pyrazine, m.p. 260° C. with decomposition, can be prepared by reacting potassium borohydride with 6-(5-methyl-1,8-naphthyridin-2-yl)-5,7-dioxo-6,7-dihydro-5H-pyrrolo[3,4-b]pyrazine in a mixture of dioxan and water (97—3 by volume) at a temperature of about 20° C.

6-(5-Methyl-1,8-naphthyridin-2-yl)-5,7-dioxo-6,7-dihydro-5H-pyrrolo [3,4-b]pyrazine can be prepared by adding dicyclohexylcarbodiimide (258 g.) to a suspension of 3-(5-methyl-1,8-naphthyridin-2-yl)carbamoyl-pyrazine-2-carboxylic acid (77 g.) in anhydrous dimethylformamide (2,500 cc.). The reaction mixture is then stirred for 72 hours at a temperature of about 20° C. The dicyclohexylurea which has crystallised is then filtered off and washed with dimethylformamide (300 cc.) and diisopropyl ether (200 cc.). Diisopropyl ether (25 liters) is then added to the filtrate. The product which crystallises is filtered off and then washed with diisopropyl ether (2,000 cc.) to yield, after drying, 6-(5-methyl-1,8-naphthyridin-2-yl)-5,7-dioxo-6,7-dihydro-5H-pyrrolo[3,4-b]pyrazine (60.9 g.), which melts with decomposition at 265° C.

3-(5-Methyl-1,8-naphthyridin-2-yl)carbamoylpyrazine-2-carboxylic acid, m.p. 265° C. with decomposition, can be prepared by condensing pyrazine-2,3-dicarboxylic acid anhydride with 2-amino-5-methyl-1,8-naphthyridine in refluxing acetonitrile.

2-Amino-5-methyl-1,8-naphthyridine can be prepared according to the method described by E. V. Brown, J. Org. Chem. 30, 1607 (1965).

Pyrazine-2,3-dicarboxylic acid anhydride can be prepared according to the method described by S. Gabriel and A. Sonn, Chem. Ber., 40, 4850 (1907).

EXAMPLE 9

Sodium hydride (50% dispersion in mineral oil) (1.83 g.) is added all at once to a suspension of 7-hydroxy-6-(7-chloro-1,8-naphthyridin-2-yl)-5-oxo-pyrrolo[3,4-b]pyridine (5.4 g.) in anhydrous dimethylformamide (55 cc.). When the evolution of gas has ceased, a solution of 1-chlorocarbonyl-4-methylpiperazine (6.2 g.) in anhydrous dimethylformamide (62 cc.) is added over the course of 5 minutes. The reaction mixture is stirred for 2 hours at a temperature of about 20° C. and then anhydrous hexamethylphosphotriamide (70 cc.) is added. After standing for 18 hours, the reaction mixture is poured into ice-water (550 cc.). The precipitate which appears is filtered off, washed with water (4 cc.) and dried; a crude product (2.6 g.) is thus obtained. The aqueous filtrate is extracted three times with methylene chloride (100 cc.). The combined extracts are washed with water (150 cc.), dried over sodium sulphate and concentrated to a volume of 50 cc. Diisopropyl ether (110 cc.) is then added, and the product which crystallises is filtered off; a crude product (1.1 g.) is thus obtained.

All the crude product (3.7 g.) is dissolved in methylene chloride (90 cc.) and the solution obtained is passed through a column of silica gel (37 g.). Elution is first carried out with methylene chloride (6 × 90 cc.) and then with a mixture (3 × 40 cc.) of methylene chloride and methanol (50—50 by volume). The last three fractions are concentrated to dryness and a wet product (3.7 g.) is obtained which is recrystallised from the dimethyl ether of glycol (600 cc.). 6-(7-Chloro-1,8-naphthyridin-2-yl)-7-(4-methylpiperazin-1-yl)-carbonyloxy-5-oxo-pyrrolo[3,4-b]pyridine (1.85 g.), melting at 270° C., is thus obtained.

7-Hydroxy-6-(7-chloro-1,8-naphthyridin-2-yl)-5-oxo-pyrrolo[3,4-b]pyridine can be prepared in the following way: Preparation of 2-(7-hydroxy-1,8-naphthyridin-2-yl)-quinolinimide (31.6 g.), m.p. 364° C., from 2-amino-7-hydroxy-1,8-naphthyridine (24.2 g.), quinolinic anhydride (45 g.) in acetic acid (120 cc.) and acetic anhydride (45 cc.) at 130°–135° C. for 1 hour. Preparation of 2-(7-chloro-1,8-naphthyridin-2-yl)quinolinimide (11.4 g.), m.p. 278° C., from 2-(7-hydroxy-1,8-naphthyridin-2-yl)quinolinimio (14g.) in phosphorous oxychloride (80 cc.) and dimethylformamide (2 cc.) for 1 hour at 95°–97° C. Preparation of 6-(7-chloro-1,8-naphthyridin-2-yl)-7-hydroxy-5-oxo-pyrrolo[3,4-b]pyridine (7.1 g.), m.p. 290° C., from 2-(7-chloro-1,8-naphthyridin-2-yl)quinolinimide (10.4 g.) and potassium borohydride (1.36 g.) in a mixture (410 cc.) (50—50 by volume) of methanol and dioxan at 10°–15° C. for 30 minutes.

EXAMPLE 10

Following the procedure of Example 9 but starting with a suspension of 6-(7-methyl-1,8-naphthyridin-2-yl)-7-hydroxy-5-oxo-pyrrolo[3,4-b]pyridine (2.7 g.) in anhydrous tetrahydrofuran (27 cc.), sodium hydride (50% dispersion in mineral oil) (0.885 g.) and 1chloro-carbonyl-4-methylpiperazine (3 g.) dissolved in anhydrous tetrahydrofuran (30 cc.), a reaction mixture is obtained which is poured into ice-water (210 cc.). The mixture is extracted with methylene chloride (3 × 400 cc.). The combined extracts are dried over potassium carbonate and are concentrated to dryness. A residue weighing 4.9 g. is thus obtained and is triturated with diisopropyl ether (60 cc.). The precipitate which appears is filtered off. The resulting product (3.6 g.) is dissolved in methylene chloride (72 cc.), and the solution is passed through a column of silica gel (36 g.). Elution is carried out successively with methylene chloride (3 × 500 cc.), a mixture (3 × 500 cc.) of methylene chloride and ethyl acetate (50—50 by volume), pure ethyl acetate (3 × 500 cc.) and a mixture (4 × 500 cc.) of ethyl acetate and methanol (90–10 by volume). The last four eluates are concentrated to dryness and the residue obtained is recrystallised from acetonitrile (58 cc.). 6-(7-Methyl-1,8-naphthyridin-2-yl)-7-(4-methylpiperazin-1-yl)carbonyloxy-5-oxo-pyrrolo[3,4-b]pyridine (1.12 g.), melting at 226° C., is thus obtained.

6-(7-Methyl-1,8-naphthyridin-2-yl)-7-hydroxy-5-oxo-pyrrolo[3,4-b]pyridine can be prepared in the following way:

Preparation of 3-N-(7-methyl-1,8-naphthyridin-2-yl)carbamoyl-pyridine-2-carboxylic acid by heating 2-amino-7-methyl-1,8-naphthyridine (10.6 g.) and quinolinic anhydride (10.9 g.) in acetonitrile (200 cc.) under reflux for 15 minutes. A product (16.1 g.), which melts at 220° C., is thus obtained. Preparation of (7-methyl-1,8-naphthyridin-2-yl)quinolinimide by treating the aforedsaid acid with acetyl chloride (2.8 cc.) in acetic acid (40 cc.). The mixture is kept at 85° C. for 30 minutes and is then cooled and filtered. A product (5.2 g.), melting at 270° C., is collected. Preparation of 6-(7-methyl-1,8-naphthyridin-2-yl)-7-hydroxy-5-oxo-pyrrolo[3,4-b]pyridine (2.7 g.), m.p. 260° C., from 2-(7-methyl-1,8-naphthyridin-2-yl)quinolinimido (3.7 g.) and sodium borohydride (0.69 g.) in methanol (38 cc.).

EXAMPLE 11

4-Methylpiperazine (8 g.) is added all at once to a suspension of 2-(1,8-naphthyridin-2-yl)-3-phenoxycarbonyloxy-isoindolin-1-one (5.6 g.) in acetonitrile (100 cc.). The solution obtained is stirred for 6 hours at a temperature of about 20° C. The reaction mixture is poured into a suspension of ice (100 g.) in methylene chloride (300 cc.). An 8% aqueous solution of sodium bicarbonate (200 cc.) is added to the suspension obtained. The organic phase is decanted and the aqueous phase is extracted with methylene chloride (400 cc.). The combined organic phases are dried over anhydrous potassium carbonate (10 g.) and concentrated to dryness. The oily residue (8 g.) is taken up in refluxing diisopropyl ether (100 cc.). On cooling the solution, crystals are deposited and are filtered off. 3-(4-Methylpiperazin-1-yl)carbonyloxy-2-(1,8-naphthyridin-2-yl)isoindolin-1-one (2.9 g.), which melts at 183° C., is thus obtained.

2-(1,8-Naphthyridin-2-yl)-3-phenoxycarbonyloxy-isoindolin-1-one can be prepared in the following way:

Preparation of 2-amino-1,8-naphthyridine, m.p. 141° C., according to W. W. Paudler and T. J. Kress, J. Org. Chem., 33, 1384 (1968). Preparation of 2-(1,8-naphthyridin-2-yl)phthalimide (8.6 g.), m.p. 250° C., by reacting 2-amino-1,8-naphthyridine (9.9 g.) with phthalic anhydride (10.2 g.) in dimethylformamide (75 cc.) at 150° C. for 1 hour 30 minutes. Preparation of 2-(1,8-naphthyridin-2-yl)-3-hydroxy-isoindolin-1-one (6.7 g.), m.p. 228° C., by reacting potassium borohydride (1.27 g.) with 2-(1,8-naphthyridin-2-yl)-phthalimide (8.6 g.) in dioxan (78 cc.) and a saturated aqueous solution of disodium phosphate (15.6 cc.) at 20° C. Preparation of 2-(1,8-naphthyridin-2-yl)-3-phenoxycarbonyloxy-isoindolin-1-one (5.6 g.), m.p. 110°-112° C., by reacting phenyl chloroformate (5.6 g.) with 2-(1,8-naphthyridin-2-yl)-3-hydroxy-isoindolin-1-one 3.9 g.) in anhydrous pyridine (70 cc.) at a temperature of about 20° C.

EXAMPLE 12

Following the procedure of Example 11 but starting with 2-(7-methyl-1,8-naphthyridin-2-yl)-3-phenoxycarbonyloxy-isoindolin-1-one (4.9 g.) and 4-methylpiperazine (6 g.) in acetonitrile (40 cc.) and stirring the reaction mixture for 24 hours at 25° C., a crude product (4.2 g.) is obtained. This product is triturated in diethyl ether (42 cc.) and then recrystallised from diisopropyl ether (300 cc.). 2-(7-Methyl-1,8-naphthyridin-2-yl)-3-(4-methylpiperazin-1-yl)carbonloxy-isoindolin-1-one (1.1 g.), melting at 190° C., is thus obtained.

2-(7-Methyl-1,8-naphthyridin-2-yl)-3-phenoxycarbonyloxy-isoindolin-1-one can be prepared in the following way: Preparation of 2-amino-7-methyl-1,8-naphthyridine, m.p. 186°-187° C., according to E. V. Brown, J. Org. Chem., 30, 1607 (1965). Preparation of 2-(7-methyl-1,8-naphthyridin-2-yl)phthalimide (5.4 g.) by reacting 7-methyl-2-amino-1,8-naphthyridine (3.18 g.) with phthalic anhydride (2.96 g.) in diphenyl ether (60 cc.) for 1 hour at 170° C. Preparation of 2-(7-methyl-1,8-naphthyridin-2-yl)-3-hydroxy-isoindolin-1-one (5.8 g.), m.p. 208° C., by reacting potassium borohydride (0.9 g.) with 2-(7-methyl-1,8-naphthyridin-2-yl)phthalimide (6.2 g.) in a mixture (60 cc.) of methanol and dioxan (50-50 by volume). Preparation of 2-(7-methyl-1,8-naphthyridin-2-yl)-3-phenoxycarbonyloxy-isoindolin-1-one (4.9 g.), m.p. 220° C. with decomposition, by reacting phenyl chloroformate (9.2 g.) with 2-(7-methyl-1,8-naphthyridin-2-yl)-3-hydroxy-isoindolin-1-one (5.8 g.) in anhydrous pyridine (160 cc.) at 5° C. for 15 minutes and then for 1½ hours at 25° C.

EXAMPLE 13

The procedure of Example 11 is followed but starting with 2-(7-chloro-1,8-naphthyridin-2-yl)-5-chloro-3-phenoxycarbonyloxy-isoindolin-1-one (1.25 g.) and 4-methylpiperazine (1.07 g.) in acetonitrile (33 cc.) and stirring for 24 hours at a temperature of about 20° C. From the reaction mixture, the resulting precipitate is filtered off and washed successively with acetonitrile (6 cc.) and diethyl ether (6 cc.). The product obtained (0.93 g.) is dissolved in methylene chloride (35 cc.), and the solution passed through a column of silica gel (10 g.). Elution is carried out with methylene chloride (16 × 20 cc.); the corresponding eluates are discarded. Elution is the carried out with ethyl acetate (5 × 20 cc.); the corresponding eluates are combined and concentrated under reduced pressure. A crystalline residue (0.9 g.) is obtained and is suspended in ethyl acetate (20 cc.). The crystals are filtered off and dried to yield 3-(4-methylpiperasin-1-yl)carbonyloxy-5-chloro-2-(7-chloro-1,8-naphthyridin-2-yl)isoindolin-1-one (0.75 g.) melting at 255° C.

2-(7-Chloro-1,8-naphthyridin-2-yl)-3-phenoxycarbonyloxy-5-chloro-isoindolin-1-one can be prepared in the following way: Preparation of 4-chlorophthalic anhydride, m.p. 96° C., according to E. E. Ayling, J. Chem. Soc., 1929, 253. Preparation of 2-amino-7-hydroxy-1,8-naphthyridine, m.p. 300°-305° C., according to S. Carboni et al, Ann. Chim. (Roma), 54, 883 (1964). Preparation of 2-(7-hydroxy-1,8-naphthyridin-2-yl)-5-chlorophthalimide (7 g.), m.p. 320° C., by reacting 2-amino-7-hydroxy-1,8-naphthyridine (9.5 g.) with 4-chlorophthalic anhydride (21.5 g.) in acetic acid (450 cc.) for 1 hour at 116° C. Preparation of 2-(7-chloro-1,8-naphthyridin-2-yl)-5-chlorophthalimide (6.4 g.), m.p. 280° C., by reacting phosphorus oxychloride (70 cc.) with 2-(7-hydroxy-1,8-naphthyridin-2-yl)-5-chlorophthalimide (7 g.) in the presence of dimethylformamide (0.7 cc.). By reacting potassium borohydride (0.75 g.) with 2-(7-chloro-1,8-naphthyridin-2-yl)-5-chlorophthalimide (6.4 g.) in a mixture (300 cc.) of dioxan and methanol (50—50 by volume, a mixture (5.2 g.) of 2-(7-chloro-1,8-naphthyridin-2-yl)-5-chloro-3-hydroxy-isoindolin-1-one and 2-(7-chloro-1,8-naphthyridin-2-yl)-6-chloro-3-hydroxy-isoindolin-1-one is obtained. This mixture is recrystallised firstly from dichloroethane (700 cc.) and then a second time from the same solvent (315 cc.). A product (1.51 g.) is thus obtained and is recrystallised successively from bromoform (38 cc.) and then from a mixture (104.5 cc.) of dichloroethane and ethanol (91-9 by volume). 2-(7-Chloro-1,8-naphthyridin-2-yl)-5-chloro-3-hydroxy-isoindolin-1-one (0.65 g.) is thus obtained. Preparation of 2-(7-chloro-1,8-naphthyridin-2-yl)-5-chloro-3-phenoxycarbonyloxy-isoindolin-1-one (1.6 g.), m.p. 220-230° C., from 2-(7-chloro-1,8-naphthyridin-2-yl)-5-chloro-3-hydroxy-isoindolin-1-one (1 g.) and phenyl chloroformate (1.36 g.) in anhydrous pyridine (15 cc.).

EXAMPLE 14

The procedure of Example 11 is followed but starting with 2-(5-chloro-1,8-naphthyridin-2-yl)-3-phenoxycarbonyloxy-isoindolin-1-one (6.7 g.), 4-methylpiperazine (15.8 g.) and dimethylformamide (32 cc.) and stirring for 15 minutes at 23° C. The reaction mixture is then diluted by adding diisopropyl ether (320 cc.). The precipitate is filtered off, washed with diisopropyl ether (3 × 30 cc.) and then dried. A product (3.8 g.) is obtained which is recrystallised from acetonitrile (300 cc.) to yield 2-(5-chloro-1,8-naphthyridin-2-yl)-3-(4-methylpiperazin-1-yl)carbonyloxy-isoindolin-1-one (2.9 g.) melting at 240° C.

2-(5-Chloro-1,8-naphthyridin-2-yl)-3-phenoxycarbonyloxy-isoindolin-1-one can be prepared in the following way:

Preparation of 2-amino-5-hydroxy-1,8-naphthyridine, m.p. 300°-305° C., according to S. Carboni et al, Gazz. Chim. Ital. 101, 136 (1971). Preparation of 2-(5-hydroxy-1,8-naphthyridin-2-yl)-phthalimide (9.9 g.), m.p. 310° C., by reacting phthalic anhydride (17.8 g.) with 2-amino-5-hydroxy-1,8-naphthyridine (9.65 g.) in acetic acid (150 cc.) and acetic anhydride (30 cc.) at 124° C. for 2 hours. Preparation of 2-(5-chloro-1,8-naphthyridin-2-yl)-phthalimide (6.1 g.), m.p. 280° C., by reacting phosphorus oxychloride (90 cc.) with 2-(5-hydroxy-1,8-naphthyridin-2-yl)phthalimide (9 g.) in the presence of dimethylformamide (3 cc.) for 1 hour at 107° C.

Preparation of 2-(5-chloro-1,8-naphthyridin-2-yl)-3-hydroxy-isoindolin-1-one (5.1 g.), m.p. 260°-262° C., by reacting potassium borohydride (0.88 g.) with 2-(5-chloro-1,8-naphthyridin-2-yl)phthalimide (5.95 g.) in a mixture (65 cc.) of methanol and dioxan (50-50 by volume) at 21° C. for 24 hours. Preparation of 2-(5-chloro-1,8-naphthyridin-2-yl)-3-phenoxycarbonyloxy-isoindolin-1-one (6.7 g.), m.p. 212° C., by reacting phenyl chloroformate (7.4 g.) with 2-(5-chloro-1,8-naphthyridin-2- yl)-3-hydroxy-isoindolin-1-one (4.9 g.) in anhydrous pyridine (120 cc.) between 3° and 6° C. for 18 hours.

EXAMPLE 15

Anhydrous piperazine (5.15 g.) is added to a suspension of 2-(7-chloro-1,8-naphthyridin-2-yl)-3-phenoxycarbonyloxy-isoindolin-1-one (5.2 g.) in acetonitrile (32 cc.). The reaction mixture is stirred for 1 hour at a temperature of about 20° C. and diisopropyl ether (150 cc.) is then added. The insoluble product is filtered off and washed with a mixture (20 cc.) of acetonitrile and diisopropyl ether (50—50 by volume) and then with diisopropyl ether (50 cc.). After recrystallisation of the product thus obtained from a mixture (160 cc.) of acetonitrile and methanol (90-10 by volume), 2-(7-chloro-1,8-naphthyridin-2-yl)-3-(piperazin-1-yl)carbonyloxy-isoindolin-1-one (2.4 g.), melting with decomposition at 245° C., is obtained.

2-(7-Chloro-1,8-naphthyridin-2-yl)-3-phenoxycarbonyloxy-isoindolin-1-one can be prepared in the following way:

Phenyl chloroformate (126 g.) is added to a suspension of 2-(7-chloro-1,8-naphthyridin-2-yl)-3-hydroxyisoindolin-1-one (86.5 g.) in pyridine (980 cc.), whilst keeping the temperature at about 25° C. The reaction mixture is then stirred for 3 hours at a temperature of about 20° C. and is thereafter poured into ice-water (9,000 cc.). The product which crystallises is filtered off and washed with water (6 × 500 cc.) and then with acetonitrile (3 × 200 cc.). After drying, 2-(7-chloro-1,8-naphthyridin-2-yl)-3-phenoxycarbonyloxy-isoindolin-1-one (96.7 g.), which melts with decomposition at 235° C., is obtained.

2-(7-Chloro-1,8-naphthyridin-2-yl)-3-hydroxyisoindolin-1-one can be prepared as described in Example 1.

EXAMPLE 16

Following the procedure of Example 15 but starting with 2-(7-chloro-1,8-naphthyridin-2-yl)-3-phenoxycarbonyloxy-isoindolin-1-one (3.45 g.) and 1-(2-hydroxyethyl)piperazine (5.2 g.) in acetonitrile (21 cc.), 2-(7-chloro-1,8-naphthyridin-2-yl)-3-[4-(2-hydroxyethyl)-piperazin-1-yl]carbonyloxy-isoindolin-1-one (2 g.) melting at 179°–180° C., is obtained.

EXAMPLE 17

Following the procedure of Example 15 but starting with 2-(7-chloro-1,8-naphthyridin-2-yl)-3-phenoxycarbonyloxy-isoindolin-1-one (3.45 g.) and 1-allylpiperazine (5.05 g.) in acetonitrile (21 cc.), 3-(4-allylpiperazin-1-yl)carbonyloxy-2-(7-chloro-1,8-naphthyridin-2-yl)isoindolin-1-one (1.65 g.), melting at 186°–187° C., is obtained.

EXAMPLE 18

Following the procedure of Example 15 but starting with 2-(7-chloro-1,8-naphthyridin-2-yl)-3-phenoxycarbonyloxy-isoindolin-1-one (2.58 g.) and 1-ethylpiperazine (3.42 g.) in acetonitrile (16 cc.), 2-(7-chloro-1,8-naphthyridin-2-yl)-3-(4-ethylpiperazin-1-yl)-carbonyloxy-isoindolin-1-one (1.4 g.), melting at 195° C., is obtained.

EXAMPLE 19

Following the procedure of Example 15 but starting with 2-(7-chloro-1,8-naphthyridin-2-yl)-3-phenoxycarbonyloxy-isoindolin-1-one (4.32 g.) and 1-propargylpiperazine (6.2 g.) in acetonitrile (27 cc.), 2-(7-chloro-1,8-naphthyridin-2-yl)-3-(4-propargylpiperazin-1-yl)carbonyloxy-isoindolin-1-one (2.05 g.), melting at 210° C., is obtained.

EXAMPLE 20

Following the procedure of Example 15 but starting with 2-(7-chloro-1,8-naphthyridin-2-yl)-3-phenoxycarbonyloxy-isoindolin-1-one (2.47 g.) and 1-isopropylpiperazine (3.66 g.) in acetonitrile (15 cc.), 2-(7-chloro-1,8-naphthyridin-2-yl)-3-(4-isopropyl-piperazin-1-yl)carbonyloxy-isoindolin-1-one (2.25 g.), melting at 203°–204° C., is obtained.

EXAMPLE 21

Following the procedure of Example 15 but starting with 2-(7-chloro-1,8-naphthyridin-2-yl)-3-phenoxycarbonyloxy-isoindolin-1-one (9.9 g.) and 1-phenylpiperazine (18.6 g.) in acetonitrile (75 cc.), 2-(7-chloro-1,8-naphthyridin-2-yl)-3-(4-phenylpiperazin-1-yl)carbonyloxy-isoindolin-1-one (1.8 g.), melting at 217° C., is obtained.

EXAMPLE 22

Following the procedure of Example 15 but starting with 2-(7-chloro-1,8-naphthyridin-2-yl)-3-phenoxycarbonyloxy-isoindolin-1-one (5.1 g.) and 1-t.-butylpiperazine (5 g.) in acetonitrile (31 cc.), 2-(7-chloro-1,8-naphthyridin-2-yl)-3-(4-t.-butylpiperazin-1-yl)carbonyloxy-isoindolin-1-one (3.3 g.), melting at 240° C., is obtained.

1-t.-Butylpiperazine can be prepared in the following way:

A solution (447 cc.) of sodium ethoxide in ethanol of concentration 1.34 moles per litre, followed by a solution (1,305 cc.) of ammonia in ethanol of concentration 4.6 moles per litre, are added to a suspension of N,N-bis(2-chloroethyl)butylamine hydrochloride (140.7 g.) in ethanol (750 cc.). The reaction mixture is then heated at a temperature of about 60° C. for 1 hour, whilst keeping the ammonia refluxing by means of a condensor containing solid carbon dioxide. The amonia is then allowed to dissipate, and the reaction mixture is cooled to a temperature of about 20° C. under a stream of nitrogen. A solution (894 cc.) of sodium ethoxide in ethanol of concentration 1.34 moles per litre is then added. The sodium chloride which precipitates is filtered off and then washed with ethanol (150 cc.). The filtrate is concentrated to dryness under reduced pressure and the residue obtained is taken up in diethyl ether (300 cc.). The insoluble product is filtered off and washed with diethyl ether (60 cc.). The filtrate is concentrated to dryness and then distilled under reduced pressure. 1-t.-Butylpiperazine (8.8 g.), which boils at 85°–86° C. under a pressure of 28 mm. Hg, is thus obtained.

N,N-bis(2-Chloroethyl)butylamine hydrochloride can be prepared according to the method described by A. Katritsky, J. Chem. Soc. B, 556 (1966).

EXAMPLE 23

A 3.16N solution (6.7 cc.) of sodium methoxide in methanol is added to a suspension of 1-methylpiperazine-1-oxide dihydrochloride (2.0 g.) in anhydrous methanol (10 cc.). After stirring for 10 minutes at 25° C., the suspension is treated with decolourinsing charcoal (0.1 g.) and then filtered. The methanolic filtrate is evaporated under reduced pressure (20 mm.Hg) at 40° C. maximum. The oily residue (2.0 g.) is dissolved in anhydrous acetonitrile (50 cc.) and 2-(7-chloro-1,8-naphthyridin-2-yl)-3-phenoxycarbonyloxy-isoindolin- 1-one (2.15 g.) is added. The reaction mixture is heated for 4 hours at 50° C. and then stirred for 48 hours at a temperature of about 25° C., filtered and concentrated under reduced pressure. The residue (3.8 g.) is dissolved in methylene chloride (50 cc.). The solution is passed through a column of Merck silica (0.02-0.05) (60 g.). Elution is carried out successively with methylene chloride (50 cc.), ethyl acetate (50 cc.), a mixture (50 cc.) of ethyl acetate and methanol (80 —20 by volume), a mixture (50 cc.) of ethyl acetate mand methanol (50—50 by volume), and finally with the same mixture of solvents (100 cc.). This last fraction is evaporated under reduced pressure. The residue obtained (0.9 g., m.p. about 200° C.) is dissolved in acetonitrile (10 cc.) and distilled water (1 cc.), near the boiling point. After cooling to 2° C., the crystals which have appeared are filtered off, washed with ice-cold acetonitrile (0.5 cc.) and dried under reduced pressure (20 mm.Hg). 4-{-[2-(7-chloro-1,8-naphthyridin-2-yl)-3-oxo-Isoindolin-1-yl]oxycarbonyl}-1-methyl-piperazine-1-oxide dihydrate (0.62 g.), melting at about 200° C. (decomposition), is obtained.

1-Methylpiperazine-1-oxide dihydrochloride can be prepared in the following way:

Preparation of t.-butyl (4-methylpiperazin-1-yl)carboxylate (as an oil; 15.0 g.) by reacting t.-butyl azidoformate (12.9 g.) with 1-methylpiperazine (9.5 g.) in water (30 cc.) and tetrahydrofuran (15 cc.), and gradually adding 5N sodium hydroxide solution (19 cc.) at a temperature of about 20 C. Preparation of 1-methyl-4-t.-butoxycarbonyl-piperazine-1-oxide hydrochloride (8.7 g.), m.p. 233° C., by reacting 4-nitroperbenzoic acid (34.0 g.) with t.-butyl (4-methylpiperazin-1-yl)-carboxylate (24.2 g.) in anhydrous chloroform (240 cc.), at a temperature not exceeding 40° C. Preparation of 1-methylpiperazine-1-oxide dihydrochloride (5.5 g.), m.p. 205° C., by reacting anhydrous gaseous hydrogen chloride (2.35 g.) with 1-methyl-4-t.-butoxycabonyl-piperazine-1-oxide hydrochloride (8.1 g.) in anhydrous ethanol (60 cc.), under reflux for 30 minutes.

EXAMPLE 24

1-Methylpiperazine (5.75 cc.) is added to a suspension of 6-(7-chloro-1,8-naphthyridin-2-yl)-7-oxo-5-phenoxycarbonyloxy-6,7-dihydro-5H-pyrrolo[3,4-b]-pyrazine (5 g.) in acetonitrile (31 cc.). The reaction mixture is stirred for 1 hour at a temperature of about 20° C. and diisopropyl ether (50 cc.) is then added. The suspension obtained is then poured into diisopropyl ether (300 cc.) and the insoluble product is filtered off and washed with diisopropyl ether (40 cc.). After drying, a product (3.6 g.), which melts at about 185° C., is obtained and is dissolved in methylene chloride (150 cc.). The resulting solution is filtered over silica gel (95 g.) in a column 3.2 cm in diameter. Elution is carried out successively with methylene chloride (1,000 cc.), a mixture (500 cc.) of methylene chloride and ethyl acetate (72-25 by volume), a mixture (300 cc.) of methylene chloride and ethyl acetate (50—50 by volume) and pure ethyl acetate (1,500 cc.). These eluates are discarded. Elution is then carried out with a mixture (1,750 cc.) of ethyl acetate and methanol (90—10 by volume); the corresponding eluate is concentrated to dryness under reduced pressure. On recrystallising the residue from acetonitrile (38 cc.), 6-(7-chloro-1,8-naphthyridin-2-yl)-5-(4-methylpiperazin-1-yl)carbonyloxy-7-oxo-6,7-dihydro-5H-pyrrolo[3,4-b]pyrazine (1.3 g.), melting at 245° C., is obtained.

6-(7-Chloro-1,8-naphthyridin-2-yl)-7-oxo-5-phenoxycarbonyloxy-6,7-dihydro-5H-pyrrolo[3,4-b]pyrazine can be prepared by adding phenyl chloroformate (9.4 g.) to a suspension of 6-(7-chloro-1,8-naphthyridin-2-yl)-5-hydroxy-7-oxo-6,7-dihydro-5H-pyrrolo[3,4-b]pyrazine (6.3 g.) in anhydrous pyridine (63 cc.), with stirring and whilst keeping the temperature at about 5° C. When the addition is complete, the reaction mixture is gradually heated to 60° C. and this temperature is maintained for 1 hour. The reaction mixture is cooled and is then poured into distilled water (350 cc.) whilst keeping the temperature at about 10° C. The insoluble product is filtered off, and washed successively with water (120 cc.), acetonitrile (40 cc.) and diisopropyl ether (40 cc.). After drying, 6-(7-chloro-1,8-naphthyridin-2-yl)-7-oxo-5-phenoxycarbonyloxy-6,7-dihydro-5H-pyrrolo[3,4-b]pyrazine (7.2 g.), melting at 270° C., is obtained.

6-(7-Chloro-1,8-naphthyridin-2-yl)-5-hydroxy-7-oxo-6,7-dihydro-5H-pyrrolo[3,4-b]pyrazine can be prepared by adding potassium borohydride (0.97 g.) to a suspension of 6-(7-chloro-1,8-naphthyridin-2-yl)-5,7-dioxo-6,7-dihydro-5H-pyrrolo[3,4-b]pyrazine (7.45 g.) in a mixture (288 cc.) of dioxan and methanol (50—50 by volume), with stirring and whilst keeping the temperature at about 3° C. After stirring for 2 hours at a temperature of about 3° C., the insoluble product is filtered off and washed successively with a mixture (24 cc.) of dioxan and methanol (50—50 by volume), water (24 cc.), a mixture (24 cc.) of dioxan and methanol (50—50 by volume) and diisopropyl ether (12 cc.). After drying, 6-(7-chloro-1,8-naphthyridin-2-yl)-5-hydroxy-7-oxo-6,7-dihydro-5H-pyrrolo[3,4-b]-pyrazine (5.3 g.), melting with decomposition at 270° C., is obtained.

6-(7-Chloro-1,8-naphthyridin-2-yl)-5,7-dioxo-6,7-dihydro-5H-pyrrolo[3,4-b]pyrazine can be prepared by adding 6-(7-hydroxy-1,8-naphthyridin-2-yl)-5,7-dioxo-6,7-dihydro-5H-pyrrolo[3,4-b]pyrazine (32 g.) gradually, and at a temperature of about 15° C., to a solution of dimethylformamide (3.8 cc.) in phosphorus oxychloride (128 cc.). When the addition is complete, the reaction mixture is heated under reflux for half an hour and is then cooled and poured in samll portions into crushed ice (1.3 kg.). The insoluble product is filtered off and then washed with water until the wash liquors are at pH 5. After drying, 6-(7-chloro-1,8-naphthyridin-2-yl)-5,7-dioxo-6,7-dihydro-5H-pyrrolo[3,4-b]pyrazine (21.3 g.), melting with decomposition at about 340° C., is obtained.

6-(7-Hydroxy-1,8-naphthyridin-2-yl)-5,7-dioxo-6,7-dihydro-5H-pyrrolo[3,4-b]pyrazine can be prepared by heating under reflux a suspension of 2-amino-7-hydroxy-1,8-naphthyridine (22.4 g.) and pyrazine-2,3-dicarboxylic acid anhydride (23 g.) in acetic acid (280 cc.). After refluxing for 1 hour, the reaction mixture is cooled to a temperature of about 30° C, and acetic anhydride (280 cc.) is added. The reaction mixture is again heated under reflux for 10 minutes and is then cooled to a temperature of about 20° C. The insoluble product is filtered off and then washed with acetic acid (40 cc.) and diisopropyl ether (200 cc.). After drying, 6-(7-hydroxy-1,8-naphthyridin-2-yl)-5,7-dioxo-6,7-dihydro-5H-pyrrolo[3,4-b]pyrazine (32.1 g.), melting at 373° C., is obtained.

2-Amino-7-hydroxy-1,8-naphthyridine can be prepared according to the method described by S. Carboni et al, Gazz. Chim. Ital., 95, 1498 (1965).

EXAMPLE 25

1-Methylpiperazine (8.15 g.) is added to a suspension of 6-(7-methoxy-1,8-naphthyridin-2-yl)-7-oxo-5-phenoxycarbonyloxy-6,7-dihydro-5H-pyrrolo[3,4-b]-pyrazine (5 g.) in dimethylformamide (50 cc.). The reaction mixture is stirred for 7 minutes at a temperature of about 17° C. and diisopropyl ether (250 cc.) is then added. The insoluble product is filtered off, washed with diisopropyl ether (30 cc.) and dried. The product obtained is dissolved in methylene chloride (130 cc.), and the solution chromatographed on silica gel (90 g.) in a column 2.4 cm. in diameter. Elution is carried out successively with a mixture (130 cc.) of methylene chloride and ethyl acetate (75-25 by volume), a mixture (130 cc.) of methylene chloride and ethyl acetate (50—50 by volume), a mixture (130 cc.) of methylene chloride and ethyl acetate (25—75 by volume), pure ethyl acetate (780 cc.), a mixture (390 cc.) of ethyl acetate and methanol (98—2 by volume), a mixture (390 cc.) of ethyl acetate and methanol (96—4 by volume) and a mixture (650 cc.) of ethyl acetate and methanol (90—10 by volume). These eluates are discarded. Elution is then carried out with a mixture (1,300 cc.) of ethyl acetate and methanol (90—10 by volume). The corresponding eluate is concentrated to dryness under reduced pressure. AFter recrystallizing the residue from acetonitrile (62 cc.), 6-(7-methoxy-1,8-naphthyridin-2-yl)-5-(4-methylpiperazin-1-yl)carbonyloxy-7-oxo-6,7-dihydro-5H-pyrrolo[3,4-b]pyrazine (1.8 g.), melting at 237° C., is obtained.

6-(7-Methoxy-1,8-naphthyridin-2-yl)-7-oxo-5-phenoxycarbonyloxy-6,7-dihydro-5H-pyrrolo[3,4-b]pyrazine, m.p. 255° C., can be prepared by reacting phenyl chloroformate with 5-hydroxy-6-(7-methoxy-1,8-naphthyridin-2-yl)-7-oxo-6,7-dihydro-5H-pyrrolo[3,4-b]pyrazine in anhydrous pyridine at a temperature of about 20° C.

5-Hydroxy-6-(7-methoxy-1,8-naphthyridin-2-yl)-7-oxo-6,7-dihydro-5H-pyrrolo[3,4-b]pyrazine, m.p. 255° C., can be prepared by reacting potassium borohydride with 6-(7-methoxy-1,8-naphthyridin-2-yl)-5,7-dioxo-6,7-dihydro-5H-pyrrolo[3,4-b]pyrazine in a mixture of dioxan and water (98-2 by volume) at a temperature of about 20° C.

6-(7-Methoxy-1,8-naphthyridin-2-yl)-5,7-dioxo-6,7-dihydro-5H-pyrrolo[3,4b]pyrazine, m.p. 296° C., can be prepared by reacting pyrazine-2,3-dicarboxylic acid anhydride with 2-amino-7-methoxy-1,8-naphthyridine in acetic acid in the presence of acetic anhydride at the reflux temperature.

EXAMPLE 26

Following the procedure of Example 25 but starting with 6-(5,7-dimethyl-1,8-naphthyridin-2-yl)-7-oxo-5-phenoxycarbonyloxy-6,7-dihydro-5H-pyrrolo[3,4-b]-pyrazine (2.8 g.) and 1-methylpiperazine (7 cc.) in dimethylformamide (7 cc.), 6-(5,7-dimethyl-1,8-naphthyridin-2-yl)-5-(4-methylpiperazin-1-yl)carbonyloxy-7-oxo-6,7-dihydro-5H-pyrrolo[3,4-b]pyrazine (0.7 g.), melting at 255° C., is obtained.

6-(5,7-Dimethyl-1,8-naphthyridin-2-yl)-7-oxo-5-phenoxycarbonyloxy-6,7-dihydro-5H-pyrrolo[3,4-b]-pyrazine, m.p. 220° C., can be prepared by reacting phenyl chloroformate with 6-(5,7-dimethyl-1,8-naphthyridin-2-yl)-5-hydroxy-7-oxo-6,7-dihydro-5H-pyrrolo[3,4-b]pyrazine in anhydrous pyridine at a temperature of about 2° C.

6-(5,7-Dimethyl-1,8-naphthyridin-2-yl)-5-hydroxy-7-oxo-6,7-dihydro-5H-pyrrolo[3,4-b]pyrazine, m.p. 265° C. with decomposition, can be prepared by reacting potassium borohydride with 6-(5,7-dimethyl-1,8-naphthyridin-2-yl)-5,7-dioxo-6,7-dihydro-5H-pyrrolo-[3,4-b]pyrazine in a mixture of dioxan and water (99-1 by volume) at a temperature of about 20° C.

6-(5,7-Dimethyl-1,8-naphthyridin-2-yl)-5,7-dioxo-6,7-dihydro-5H-pyrrolo[3,4-b]pyrazine can be prepared by heating under reflux a suspension of 3-(5,7-dimethyl-1,8-naphthyridin-2-yl)carbamoyl-pyranzine-2-carboxylic acid (12 g.) in thinonyl chloride (120 cc.). When the evolution of gas has ceased, the reaction mixture is cooled to a temperature of about 5° C. and diisopropyl ether (200 cc.) is then added. The insoluble product is filtered off and washed with diisopropyl ether (60 cc.). After drying, 6-(5,7-dimethyl-1,8-naphthyridin-2-yl)-5,7-dioxo-6,7-dihydro-5H-pyrrolo[3,4-b]pyrazine (11.5 g.), melting at about 250° C. with decomposition, is obtained.

3-(5,7-Dimethyl-1,8-naphthyridin-2-yl)carbamoyl-pyrazine-2-carboxylic acid, m.p. 255° C. with decomposition, can be prepared by reacting pyrazine-2,3-dicarboxylic acid anhydride with 2-amino-5,7-dimethyl-1,8-naphthyridine in anhydrous dimethylformamide at a temperature of about 100° C.

2-Amino-5,7-dimethyl-1,8-naphthyridine, which melts at 225°-226° C., can be prepared according to the method of J. Bernstein et al, J. Amer. Chem. Soc., 69, 1151 (1947).

EXAMPLE 27

A solution of 3-chloroperbenzoic acid (1.77 g.) in chloroform (60 cc.) is added to a solution of 6-(7-chloro-1,8-naphthyridin-2-yl)-5-(4-methylpiperazin-1-yl)-carbonyloxy-7-oxo-6,7-dihydro-5H-pyrrolo[3,4-b]pyrazine (2.7 g.) in chloroform (45 cc.). The reaction mixture is stirred for 1 hour at a temperature of about 20° C. and a saturated aqueous solution of sodium bicarbonate (40 cc.) and methylene chloride (50 cc.) are then added. The aqueous layer is decanted and then washed twice with methylene chloride (50 cc.). The organic layers are combined, washed twice with water (30 cc.), dried over anhydrous sodium sulphate and then concentrated to dryness under reduced pressure. The residue is dissolved in methylene chloride (50 cc.) and the resulting solution is filtered through silica gel (25 g.) in a column 1.8 cm. in diameter. Elution is carried out successively with a mixture (620 cc.) of methylene chloride and methanol (94—6 by volume) and a mixture (190 cc.) of methylene chloride and methanol (90—10 by volume). These eluates are discarded. Elution is then carried out successively with a mixture (140 cc.) of methylene chloride and methanol (90—10 by volume), a mixture (330 cc.) of methylene chloride and methanol (85—15 by volume) and a mixture (330 cc.) of methylene chloride and methanol (80—20 by volume); the corresponding eluates are combined and concentrated to dryness under reduced pressure. After recrystallising the residue thus obtained from methanol (20 cc.), 4-{5-[6-(7-chloro-1,8-naphthyridin-2-yl)-7-oxo-6,7-dihydro-5H-pyrrolo[3,4-b]pyrazinyl]oxycarbonyl}-1-methylpiperazine-1-oxide (0.6 g.), melting with decomposition at 245° C., is obtained.

The present invention includes within its scope pharmaceutical compositions comprising, as active ingredient, at least one of the naphthyridine derivatives of general formula I, or a non-toxic acid addition salt thereof, in association with a pharmaceutical carrier or coating. The invention includes especially such preparations made up for oral, parenteral or rectal administration or local application, e.g. as ointments.

Solid compositions for oral administration include tablets pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or nonaqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteriaretaining filter, by incorporation in the compositions of sterilising agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The precentage of active ingredient in the compositions of the invention may be varied, it being necessary that it should consititue a proportion such that a suitable dosage shall be obtained. The dosage depends on the desired therapeutic effect, on the route of administration and on the duration of the treatment. In human therapy the compositions when administered orally to an adult should generally give doses between 10 mg. and 500 mg. of active substance per day. In general the physician will decide the posology considered appropriate, taking into account the age and weight and other factors intrinsic to the patient being treated.

The following Examples illustrate pharmaceutical compositions according to the invention.

EXAMPLE 28

Tablets containing 25 mg. of active product and having the following composition are prepared in accordance with the usual technique:

| | |
|---|---|
| 2-(7-chloro-1,8-naphthyridin-2-yl)-3-(4-methyl-piperazin-1-yl)carbonyloxy-isoindolin-1-one | 0.025 g. |
| starch | 0.090 g. |
| precipitated silica | 0.030 g. |
| magnesium stearate | 0.005 g. |

EXAMPLE 29

Tablets containing 25 mg. of active product and having the following composition are prepared in accordance with the usual technique:

| | |
|---|---|
| 6-(7-chloro-1,8-naphthyridin-2-yl)-7-(4-methylpiperazin-1-yl)carbonyloxy-5-oxo-pyrrolo[3,4-b]pyrazine | 0.025 g. |
| starch | 0.090 g. |
| precipitated silica | 0.030 g. |
| magnesium stearate | 0.005 g. |

We claim:
1. A naphthyridine compound of the formula:

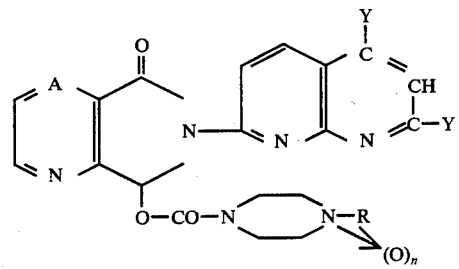

wherein each Y represents hydrogen, halogen, alkyl of 1 through 4 carbon atoms, or alkoxy of 1 through 4 carbon atoms, =A- represents =CH- or =N-, $n$ is zero and R represents alkyl of 1 through 4 carbon atoms, or $n$ is 1 and R is methyl, or a non-toxic pharmaceutically acceptable acid addition salt thereof.

2. The naphthyridine compound according to claim 1 which is 6-(7-chloro-1,8-naphthyridin-2-yl)-5-(4-methylpiperazin-1-yl)carbonyloxy-7-oxo-6,7-dihydro-5H-pyrrolo[3,4-b]pyrazine or a non-toxic pharmaceutically acceptable acid addition salt thereof.

3. A naphthyridine compound according to claim 1 wherein one Y is hydrogen and the other is chlorine, methyl, or methoxy, $n$ is zero and R is methyl.

4. The naphthyridine compound according to claim 1 which is 6-(5-methyl-1,8-naphthyridin-2-yl)-5-(4-methylpiperazin-1-yl)-carbonyloxy-7-oxo-6,7-dihydro-5H-pyrrolo[3,4-b]pyrazine or a non-toxic pharmaceutically acceptable acid addition salt thereof.

5. The naphthyridine compound according to claim 1 which is 6-(7-chloro-1,8-naphthyridin-2-yl)-7-(4-methylpiperazin-1-yl)-carbonyloxy-5-oxo-pyrrolo[3,4-b]pyridine or a non-toxic pharmaceutically acceptable acid addition salt thereof.

6. The naphthyridine compound according to claim 1 which is 6-(7-methyl-1,8-naphthyridin-2-yl)-7-(4-methylpiperazin-1-yl)-carbonyloxy-5-oxo-pyrrolo[3,4-b]pyridine or a non-toxic pharmaceutically acceptable acid addition salt thereof.

7. The naphthyridine compound according to claim 1 which is 6-(7-methoxy-1,8-naphthyridin-2-yl)-5-(4-methylpiperazin-1-yl)carbonyloxy-7-oxo-6,7-dihydro-5H-pyrrolo[3,4-b]pyrazine or a non-toxic pharmaceutically acceptable acid addition salt thereof.

8. The naphthyridine compound according to claim 1 which is 6-(5,7-dimethyl-1,8-naphthyridin-2-yl)-5-(4-methylpiperazin-1-yl)carbonyloxy-7-oxo-6,7-dihydro-5H-pyrrolo[3,4-b]-pyrazine or a non-toxic pharmaceutically acceptable acid addition salt thereof.

9. The naphthyridine compound according to claim 1 which is 4-{5-[6-(7-chloro-1,8-naphthyridin-2-yl)-7-oxo- 6,7-dihydro-5-H-pyrrolo[3,4-b]pyrazinyl]oxycarbonyl{1-methylpiperazine-1-oxide or a non-toxic pharmaceutically acceptable acid addition salt thereof.

10. The naphthyridine compound according to claim 1 which is 6-(7-chloro-1,8-naphthyridin-2-yl)-5-(4-methylpiperazin-1-yl)carbonyloxy-7-oxo-6,7-dihydro-5H-pyrrolo-[3,4-b]pyrazine or a non-toxic pharmaceutically acceptable acid addition salt thereof.

11. A pharmaceutical composition useful as a tranquilliser and anti-convulsant agent which comprises, as active ingredient, an effective amount of a naphthyridine compound of the formula depicted in claim 1 wherein the various symbols have the meanings specified in claim 1, or a non-toxic pharmaceutically acceptable acid addition salt thereof, in association with a significant amount of a pharmaceutical carrier.

* * * * *